United States Patent
Ingram

(10) Patent No.: US 11,524,098 B2
(45) Date of Patent: Dec. 13, 2022

(54) SYSTEMS AND METHODS FOR BIOFILM INOCULATION

(71) Applicant: Avent, Inc., Alpharetta, GA (US)

(72) Inventor: Aaron N. Ingram, Canton, GA (US)

(73) Assignee: Avent, Inc., Alpharetta, GA (US)

(*) Notice: Subject to any disclaimer, the term of this patent is extended or adjusted under 35 U.S.C. 154(b) by 557 days.

(21) Appl. No.: 16/569,168

(22) Filed: Sep. 12, 2019

(65) Prior Publication Data

US 2020/0086010 A1    Mar. 19, 2020

Related U.S. Application Data

(60) Provisional application No. 62/731,791, filed on Sep. 14, 2018.

(51) Int. Cl.
| | | |
|---|---|---|
| *A61J 15/00* | (2006.01) | |
| *A61L 24/00* | (2006.01) | |
| *A61L 29/16* | (2006.01) | |
| *A61L 29/00* | (2006.01) | |
| *A61L 29/08* | (2006.01) | |
| *A61M 25/00* | (2006.01) | |

(52) U.S. Cl.
CPC ............ *A61L 29/16* (2013.01); *A61J 15/0003* (2013.01); *A61J 15/0015* (2013.01); *A61J 15/0069* (2013.01); *A61L 29/005* (2013.01); *A61L 29/08* (2013.01); *A61L 2420/02* (2013.01); *A61M 2025/006* (2013.01)

(58) Field of Classification Search
CPC . A61J 15/0003; A61J 15/0069; A61J 15/0015
See application file for complete search history.

(56) References Cited

U.S. PATENT DOCUMENTS

| | | | | |
|---|---|---|---|---|
| 8,197,872 B2 * | 6/2012 | Mills | ........................ | A23G 4/10 |
| | | | | 426/583 |
| 2005/0112612 A1 * | 5/2005 | Klaenhammer | ........ | A61P 39/02 |
| | | | | 435/320.1 |
| 2009/0246184 A1 * | 10/2009 | Harel | ................... | A61K 35/742 |
| | | | | 424/93.46 |
| 2010/0120701 A1 * | 5/2010 | McCoy | .................... | C12N 9/88 |
| | | | | 435/254.2 |
| 2011/0067703 A1 * | 3/2011 | Martens | ................... | A61L 31/16 |
| | | | | 128/207.14 |
| 2013/0202571 A1 * | 8/2013 | Bhunia | ................ | A61K 35/747 |
| | | | | 424/93.4 |

FOREIGN PATENT DOCUMENTS

| | | | | | |
|---|---|---|---|---|---|
| GB | | 2544481 A | * | 5/2017 | ............... A41D 1/00 |
| RU | | 2571498 C2 | * | 12/2015 | ............. A61J 11/00 |
| WO | WO 03/082148 A1 | | | 10/2003 | |
| WO | WO-03082148 A1 | | * | 10/2003 | ............. A01N 63/00 |
| WO | WO-2008071330 A2 | | * | 6/2008 | ......... A61B 17/3415 |
| WO | WO 2009/020455 A1 | | | 2/2009 | |
| WO | WO 2016/168729 A1 | | | 10/2016 | |
| WO | WO-2016168729 A1 | | * | 10/2016 | ............... A23G 1/50 |

OTHER PUBLICATIONS

Chen et al. Probiotic *E. coli* Nissle 1917 biofilms on silicone substrates for bacterial interference against pathogen colonization. Acta Biomaterialia 50 (2017) 353-360 (Year: 2017).*
International Search Report and Written Opinion for PCT/US2019/050924, dated Dec. 17, 2019, 10 pages.

* cited by examiner

*Primary Examiner* — Cachet I Proctor
(74) *Attorney, Agent, or Firm* — Dority & Manning, P.A.

(57) ABSTRACT

Systems and methods for biofilm inoculation including a feeding tube having a distal end for placement in the gut of a patient, and a biofilm coated or otherwise provided on the distal end of the feeding tube for introducing the biofilm to the gut of the patient. In example embodiments, the biofilm can be colostrum, breast milk or one or more probiotics.

11 Claims, No Drawings

SYSTEMS AND METHODS FOR BIOFILM INOCULATION

CORRESPONDING PATENTS

This application claims priority to U.S. Provisional Patent Application No. 62/731,791, filed on Sep. 10, 2018, which is incorporated hereinafter for all purposes.

TECHNICAL FIELD

The present invention relates generally to the field of enteral feeding and nutritional delivery, and more particularly to systems and methods for introducing healthy bacteria during enteral feeding and nutritional delivery.

BACKGROUND

The occurrence of necrotizing enterocolitis (NEC) in neonates and premature infants has been and remains to be a devastating problem. Commonly, neonates can have or develop immunodeficiencies where minimal (if any) "healthy" gut microbiota exists, for example because such babies were delivered through c-section and so did not benefit from the introduction of gut bacterial through the birthing process and/or an initial feeding from the mother. It is difficult for these immunocompromised patients to fight infections that can originate in the gut when pathogenic bacteria exist and is potentially limiting the influence of the good/healthy bacteria that the gut needs as part of the body's immune system. One study shows that around 10 percent of infants born under 1500 g will develop NEC, and mortality remains as high as 30 percent for the infants that develop NEC. Accordingly, it can be seen that needs exist for systems and methods to substantially eliminate (if not entirely prevent) the development of NEC in infants (especially premature infants). It is to the provision of systems and methods for biofilm inoculation meeting these and other needs that the present invention is primarily directed.

SUMMARY

In example embodiments, the present invention provides systems and methods for biofilm inoculation.

In one aspect, the present invention relates to a feeding tube for enteral delivery having a distal end for insertion in the gut of a patient. In example embodiments, the distal end has an outer surface, an inner surface and an end surface, and wherein at least a portion of the distal end includes a biofilm. In example embodiments, the biofilm can be colostrum, breast milk and/or one or more probiotics.

In another aspect, the invention relates to a method of biofilm inoculation including providing a feeding tube; providing a quantity of colostrum or breast milk; coating or otherwise providing at least a portion of the quantity of colostrum or breast milk on at least a portion of the feeding tube; and placing at least a portion of the feeding tube in the gut of a patient. In example embodiments, the colostrum or breast milk is coated or otherwise provided on a distal end of the feeding tube, and the distal end of the feeding tube is placed in the gut of the patient.

In another aspect, the invention relates to a method for limiting the formation of pathogenic bacteria in the gut of neonatal patients. The method includes adhering a layer of pathogenically beneficial material to an insertion end of a feeding tube; inserting the insertion end of the feeding tube into the gut of a neonatal patient, the gut of the neonatal patient containing a volume of fluid; and dispersing the layer of pathogenically beneficial material from the insertion end of the feeding tube and into the volume of fluid contained within the gut of the neonatal patient.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

DETAILED DESCRIPTION OF EXAMPLE EMBODIMENTS

The present invention may be understood more readily by reference to the following detailed description of example embodiments. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Example embodiments of the present invention preferably provide for the introduction of a healthy or "good" bacteria (e.g., probiotic) biofilm within the gut of mammals, for example human babies. For example, according to example embodiments of the present invention, a biofilm is introduced into the gut of a neonate or premature infant so as to limit and/or prohibit the formation of pathogenic biofilm/ "bad" bacteria. Preferably, by introducing the biofilm (e.g., healthy bacteria) in the gut, the occurrences or likelihood of obtaining necrotizing enterocolitis (NEC) are substantially eliminated (if not entirely eliminated).

According to one example embodiment of the present invention, at least a portion of an enteral feeding or tube feeding system (e.g., feeding tube, vessel or other nutritional/medicinal delivery conduit), hereinafter referred to as a "feeding tube", comprises a biofilm. In example embodiments, the biofilm is preferably coated or otherwise provided on a portion of the feeding tube prior to placement of the feeding tube in the gastrointestinal (GI) tract or gut of a patient. Preferably, the biofilm is introduced into the gut of a patient upon initial placement of the feeding tube in the gut. In example embodiments, introducing the biofilm in the gut provides for stabilizing the gut microbiome, reducing intestinal mucosal barrier breakdown, and limiting intestinal inflammation (among a plurality of other benefits).

For example, according to one example embodiment, in the case that the neonate or premature infant has an immunodeficiency, the biofilm that is provided on at least a portion of the feeding tube can be inoculated upon placement of the feeding tube in the gut. According to another example embodiment, regardless of whether the neonate or premature infant has an immunodeficiency, the biofilm of the feeding tube can similarly be inoculated into the gut during the initial placement thereof.

Thus, according to one example embodiment of the present invention, inoculating the gut of a patient with "healthy" or "good" bacteria by means of its presence on a portion of the feeding tube that is to be exposed to the gut, the patent's gut microbiome is preferably more stable and diverse, thereby substantially eliminating (if not entirely) the occurrence or likelihood of obtaining NEC.

According to example embodiments of the present invention, the biofilm comprises colostrum or breast milk. For example, according to example embodiments, at least a portion of the feeding tube is coated with colostrum or breast milk prior to the insertion of the feeding tube in the gut of the patient. In one example, a tip section or distal end of the feeding tube is coated with colostrum or breast milk to form the biofilm, and then the distal end of the feeding tube is placed in the gut of the patient to 1) expose the biofilm to the gut and 2) to permit nutritional or medicinal fluid delivery through the feeding tube and in the gut.

In example embodiments, the distal end of the feeding tube and the colostrum or breast milk are placed within a reservoir or enclosed space (or otherwise exposed to each other) for at least some amount of time, for example, so as to allow the colostrum or breast milk to adhere, for example through gravitational and hydrodynamic forces, to the distal end of the feeding tube (e.g., to fully saturate, swab, smear, expose the distal end of the feeding tube with the colostrum or breast milk in order to form a thin film layer thereon). According to one example embodiment, at least some incubation period can be provided so as to promote further growth or development of the bacteria of the biofilm prior to placement of the distal end in the gut. The incubation period should terminate prior to other undesirable organisms colonizing the exposed surface, for example such incubation should not last longer than four hours. According to another example embodiment, after exposure or saturation of the distal end of the feeding tube with the colostrum or breast milk, the distal end of the feeding tube is placed in an environment, for example preferably between room temperature and body temperature, to promote further growth or development, or to protect from unwanted exposure to potentially damaging bacteria or pathogens.

According to one example embodiment, the distal end of the feeding tube comprises an outer surface, an inner surface (defining a lumen) and an end surface. Preferably, the colostrum or breast milk can be provided on one or more of the outer surface, inner surface or the end surface. According to some example embodiments, one or more portions of the feeding tube (including the distal end and outer, inner and end surfaces thereof) are provided with a surface treatment to attract or propagate the biofilm. The surfaces can be treated such that it is texturized so as to promote improved adherence of the biofilm. Different surface textures can be introduced by a variety of methods, for example extrusion die surface characteristics or exposure of surfaces to high voltage electrical arc, corona or other recognized surface treatment methodologies. In order to achieve optimum effectiveness, certain processing parameters such as extrusion speed, extrusion temperature, air dwell time prior to immersion bath, temperature of immersion cooling bath, and a host of similar process parameters can be adjusted. In other example embodiments, the distal end of the feeding tube (or surfaces thereof) can comprise one or more micro channels or conduits such that the biofilm remains adhered thereto. In other example embodiments, the distal end of the feeding tube is at least partially porous (or substantially porous) such that the biofilm remains thereon prior to placement of the same in the gut. Alternatively, an inert porous biodigestible seed can be inserted and pushed into the feeding tube prior to insertion to populate a film. Optionally, in other example embodiments, one or more additional procedures or steps can be provided to enhance the adherence of the biofilm with the feeding tube. For example, according to some example embodiments, direct or indirect light, heat, plasma, corona arc or other forms of energy can be provided so as to promote the adherence and/or growth of the biofilm on the feeding tube.

According to another example embodiment, the distal end of the feeding tube is exposed to one or more forms of energy, for example corona arc or other previously mentioned alternatives, prior to being coated with the colostrum or breast milk, for example, to promote an enhanced adherence of the biofilm on the feeding tube. Optionally, one or more additional procedures or step can be taken before or after exposing the feeding tube to the colostrum or breast milk to ensure the biofilm remains with the distal end of the feeding tube during placement of the same in the gut of the patient.

According to another example embodiment, at least the distal end of the feeding tube is hydrophilic or absorptive so as to allow the biofilm to adhere thereto, and for example, to prevent removal of the biofilm from the distal end of the feeding tube during the placement thereof in the gut of the patient.

According to another example embodiment of the present invention, one or more probiotics or other forms of "good" bacteria can be coated or otherwise provided on at least a portion of the feeding tube so as to introduce the same in the gut of the patient during placement of the feeding tube.

According to another example embodiment, at least the distal end of the feeding tube can be coated or exposed to one or more chemicals or materials before or after exposing the feeding tube to the colostrum or breast milk to ensure the biofilm remains with the distal end of the feeding tube during placement of the same in the gut of the patient.

According to another example embodiment, one or more additional components, films, layers or coatings can be provided at least at the distal end of the feeding tube to assist in ensuring the biofilm is introduced in the gut of the patient during initial placement of the feeding tube in the same. Such coated tubes can be stored a period of time not to exceed 72 hours.

According to another example embodiment, the present invention relates to a method of biofilm inoculation comprising providing a feeding tube; providing a quantity of colostrum or breast milk; coating or otherwise providing at least a portion of the quantity of colostrum or breast milk on at least a portion of the feeding tube; and placing at least a portion of the feeding tube in the gut of a patient. In example embodiments, the colostrum or breast milk is coated or otherwise provided on a distal end of the feeding tube, and the distal end of the feeding tube is placed in the gut of the patient.

According to another example embodiment, the present invention relates to a method of biofilm inoculation comprising: providing a feeding tube; providing a quantity of colostrum or breast milk; coating or otherwise providing at least a portion of the quantity of colostrum or breast milk on at least a portion of the feeding tube; and placing at least a portion of the feeding tube in the gut of a patient. The colostrum or breast milk can be coated or otherwise provided on a distal end of the feeding tube.

According to another example embodiment, the present invention relates to a feeding tube for enteral delivery comprising a distal end for insertion in the gut of a patient, the distal end comprising an outer surface, an inner surface and an end surface, wherein at least a portion of the distal end comprises a biofilm. The biofilm can comprise colostrum. The biofilm can comprise breast milk. The biofilm can comprise one or more probiotics. The biofilm can comprise one or more of colostrum, breast milk or one or more probiotics. At least a portion of the distal end can comprise a surface treatment so as to enhance the adherence of the biofilm.

While the invention has been described with reference to example embodiments, it will be understood by those skilled in the art that a variety of modifications, additions and deletions are within the scope of the invention, as defined by the following claims.

What is claimed is:

1. A method for limiting the formation of pathogenic bacteria in the gut of neonatal patients, the method comprising:
   adhering a layer of beneficial probiotic material to an insertion end of a feeding tube;
   inserting the insertion end of the feeding tube into the gut of a neonatal patient, the gut of the neonatal patient containing a volume of fluid; and
   dispersing the layer of beneficial probiotic material from the insertion end of the feeding tube and into the volume of fluid contained within the gut of the neonatal patient.

2. The method of claim 1, wherein the beneficial probiotic material can be one of a group consisting of human breast milk, human colostrum, and a probiotic.

3. The method of claim 1, wherein the adhering step further comprises submersing the insertion end of the feeding tube into a container of a volume of the beneficial probiotic material in liquid form.

4. The method of claim 1, wherein the adhering step further comprises causing the layer of beneficial probiotic material to coat the insertion end of the feeding tube through a combination of gravitational and hydrodynamic forces.

5. The method of claim 1, wherein the adhering step further comprises exposing the layer of beneficial probiotic material on the insertion end of the feeding tube to light energy.

6. The method of claim 1, wherein the adhering step further comprises exposing the layer of beneficial probiotic material on the insertion end of the feeding tube to room temperature.

7. The method of claim 1, wherein the insertion end of the feeding tube comprises surface texturing.

8. The method of claim 1, further comprising inserting a biodigestible seed into the insertion end of the feeding tube.

9. The method of claim 1, further comprising inserting a porous biodigestible seed into the insertion end of the feeding tube, the porous biodigestible seed absorbs a volume of the beneficial probiotic material.

10. The method of claim 1, wherein the layer of beneficial probiotic material is adhered to the insertion end of the feeding tube through hydrodynamic forces.

11. The method of claim 1, wherein the insertion end of the feeding tube comprises hydrophilic surface properties.

* * * * *